United States Patent [19]

Manogue et al.

[11] Patent Number: 5,030,372

[45] Date of Patent: Jul. 9, 1991

[54] CATALYTIC EQUILIBRATION TO IMPROVE THE RELATIVE YIELD OF SELECTED HALOCARBONS

[75] Inventors: William H. Manogue, Newark; V. N. Mallikarjuna Rao; Frank J. Weigert, both of Wilmington, all of Del.

[73] Assignee: E. I. Du Pont de Nemours and Company, Wilmington, Del.

[21] Appl. No.: 560,529

[22] Filed: Jul. 31, 1990

[51] Int. Cl.$^5$ .......................... C09K 5/02; C09K 5/04; C07C 17/00; C07C 19/08

[52] U.S. Cl. ........................................ 252/67; 252/71; 252/70; 252/68; 252/69; 252/73; 62/4; 570/151; 570/163; 570/176

[58] Field of Search ............... 570/151, 163, 176, 168; 252/70, 71, 67, 68, 69, 73; 62/4

[56] References Cited

U.S. PATENT DOCUMENTS

| | | | |
|---|---|---|---|
| 2,478,201 | 9/1949 | Miller | 570/163 |
| 2,494,064 | 3/1947 | Simons | 260/653.1 |
| 2,598,411 | 11/1948 | Miller | 570/151 |
| 2,920,112 | 1/1960 | Larson | 570/176 |
| 3,087,976 | 4/1963 | Hauptschein | 570/163 |
| 3,398,202 | 8/1968 | Foulletier | 260/653 |
| 3,787,331 | 1/1974 | Groppelli | 570/163 |
| 4,155,941 | 5/1979 | Nychka | 570/163 |
| 4,192,822 | 3/1980 | Sweeney | 570/163 |
| 4,745,237 | 5/1988 | Ballard | 570/176 |
| 4,748,284 | 5/1988 | Gozzo | 570/151 |
| 4,766,260 | 8/1988 | Manzer | 570/168 |
| 4,843,181 | 6/1989 | Gumprecht | 570/168 |
| 4,873,381 | 10/1989 | Kellner | 570/176 |
| 4,902,838 | 2/1990 | Manzer | 570/151 |
| 4,925,993 | 5/1990 | Zawalski | 570/151 |
| 4,935,558 | 6/1990 | Krespan | 570/176 |
| 4,950,815 | 8/1990 | Moore | 570/176 |

FOREIGN PATENT DOCUMENTS

| | | |
|---|---|---|
| 693851 | 9/1964 | Canada ............ 570/163 |
| 703294 | 2/1965 | Canada ............ 570/163 |
| 1039503 | 9/1958 | Fed. Rep. of Germany . |
| 2245372 | 3/1974 | Fed. Rep. of Germany . |
| 53-121710 | 10/1978 | Japan ............ 570/151 |
| 61-27375 | 6/1986 | Japan . |
| 1258630 | 10/1989 | Japan . |
| 240332 | 2/1990 | Japan . |
| 2111733 | 4/1990 | Japan . |
| 2115135 | 4/1990 | Japan . |
| 1578933 | of 0000 | United Kingdom . |
| 873212 | 7/1961 | United Kingdom . |
| 921796 | 3/1963 | United Kingdom . |

OTHER PUBLICATIONS

Miller et al., JACS 72, Rearrangement of Chlorofluorocarbons by Aluminum Chloride, Feb. 1950, pp. 705–707.

*Primary Examiner*—Paul Lieberman
*Assistant Examiner*—Kevin McCarthy

[57] ABSTRACT

Gas phase and liquid phase processes are disclosed which use interconversion of $CF_3CHFCl$ and $CF_2HCF_2Cl$ in contact with catalyst consisting essentially of halided aluminum oxide and/or aluminum halide at elevated temperatures to increase the mole ratio of one of said compounds in a composition relative to the other. Also disclosed in use of said interconversion along with hydrogenolysis in processes for producing mixtures of $CF_3CH_2F$ and $CF_2HCF_2H$ from certain compositions comprising $CF_2HCF_2Cl$ such that the mole ratio of $CF_3CH_2F$ to $CF_2HCF_2H$ in the product mixtures produced from said compositions may be increased or decreased.

12 Claims, No Drawings

CATALYTIC EQUILIBRATION TO IMPROVE THE RELATIVE YIELD OF SELECTED HALOCARBONS

FIELD OF THE INVENTION

This invention relates to the preparation of halogen substituted hydrocarbons and more particularly to the use of equilibrium reactions during preparation of halogen substituted hydrocarbons containing fluorine.

BACKGROUND OF THE INVENTION

There has been considerable recent interest in halogen substituted ethanes containing fluorine and hydrogen. Many of these materials can be used not only as blowing agents, solvents and refrigerants, but also as starting materials for preparing other useful compounds. Among the halogen substituted ethanes of note are $CF_2HCF_2Cl$ (HCFC-124a) and $CHF_2CHF_2$ (HFC-134) which can be prepared by hydrogenolysis of $CClF_2CClF_2$ (CFC-114); and $CF_3CH_2F$ (HFC-134a) and $CF_3CHClF$ (HCFC-124), which can be prepared by hydrogenolysis of $CF_3CCl_2F$ (CFC-114a). UK Patent Specification 1,578,933, for example, discloses a process for the manufacture of tetrafluoroethane characterized in that certain haloethanes having four or five fluorine atoms (e.g., $CClF_2CClF_2$, $CCl_2FCF_3$, $CClF_2CF_3$, $CHClFCF_3$, $CHF_2CClF_2$ and/or $CHF_2CF_3$) are reacted with hydrogen at an elevated temperature in the presence of a hydrogenation catalyst such as palladium supported on charcoal or palladium supported on alumina. As exemplified in UK Patent Specification 1,578,933 hydrogenation of mixtures of 2,2-dichloro-1,1,1,2-tetrafluoroethane and 1,2-dichloro-1,1,2,2-tetrafluoroethane, produce mixtures of the two isomers of tetrafluoroethane. The formation of $CHF_2CClF_2/CHClFCF_3$ byproducts is exemplified; as is the use of 2-chloro-1,1,1,2-tetrafluoroethane as a starting material to produce $CF_3CH_2F$ as the major product.

U.S. Pat. No. 4,766,260 describes an improved gas phase process for the manufacture of 1,1,1,2-tetrafluorochloroethane and 1,1,1-trifluorodichloroethane by contacting a suitable tetrahaloethylene with hydrogen fluoride in the presence of a selected metal on a high fluorine content alumina support. U.S. Pat. No. 4,766,260 discloses that intermediates formed during the course of the reaction can be recycled to the reactor for the production of additional 1,1,1-trifluorodichloroethane and 1,1,1,2-tetrafluorochloroethane; and that 1,1,1-trifluorodichloroethane can be recycled to the reactor for the production of additional 1,1,1,2-tetrafluorochloroethane when this is desired.

SUMMARY OF THE INVENTION

The present invention provides a catalytic process for interconverting the chlorofluorohydrocarbons $CF_3CHClF$ (HCFC-124) and $CClF_2CHF_2$ (HCFC-1224a), using either a liquid or gas phase reaction. In accordance with this invention, halided aluminum oxide and aluminum halides function as catalysts for the interconversion reaction; and the equilibration constant for the interconversion varies with temperature over the range of 50° C. to 475° C. with the formation of $CF_3CHClF$ becoming relatively more favored as the temperature decreases.

A gas phase process for increasing in a composition the mole ratio of one compound selected from the group consisting of $CF_3CHClF$ and $CClF_2CHF_2$ relative to the other compound of said group, is provided in accordance with this invention which comprises the steps of: (a) providing a gaseous composition comprising at least one compound of said group provided that (i) if the selected compound is $CF_3CHClF$ the mole ratio of $CF_3CHClF$ to $CClF_2CHF_2$ in said gaseous composition is less than the equilibrium ratio thereof at 50° C., and (ii) if the selected compound is $CClF_2CHF_2$, the mole ratio of $CClF_2CHF_2$ to $CF_3CHClF$ in said gaseous composition is less than the equilibrium ratio thereof at 475° C.; (b) contacting said gaseous composition with a catalyst consisting essentially of a halided aluminum oxide, an aluminum halide or mixtures thereof, for a time sufficient to provide substantial interconversion between $CF_3CHClF$ and $CClF_2CHF_2$; and (c) providing during said catalyst contact a temperature within the range of about 50° C. to 475° C. at which the mole ratio of the selected compound to the other compound increases. Preferably a halided alumina catalyst is used for this gas phase process. The halided alumina is obtained by pretreatment of alumina with a vaporizable halogen-containing compound.

A liquid phase process for increasing in a composition the mole ratio of one compound selected from the group consisting of $CF_3CHClF$ and $CClF_2CHF_2$ relative to the other compound of said group is provided in accordance with this invention which comprises the steps of: (a) providing a liquid composition comprising at least one compound of said group provided that (i) if the selected compound is $CF_3CHClF$, the mole ratio of $CF_3CHClF$ to $CClF_2CHF_2$ in said liquid composition is less than the equilibrium ratio thereof at 50° C., and (ii) if the selected compound is $CClF_2CHF_2$, the mole ratio of $CClF_2CHF_2$ to $CF_3CHClF$ in said liquid composition is less than the equilibrium ratio thereof at about 130° C.; (b) contacting said liquid composition with a catalyst consisting essentially of a halided aluminum oxide, an aluminum halide or mixtures thereof, for a time sufficient to provide substantial interconversion between $CF_3CHClF$ and $CClF_2CHF_2$; and (c) providing during said catalyst contact a temperature within the range of about 50° C. to about 130° C. at which the mole ratio of the selected compound to the other compound increases. Preferably an aluminum halide catalyst is used for this liquid phase reaction. The aluminum halide may contain Cl, F or a mixture of the two halogens.

Because the molar ratio of $CF_3CHClF$ to $CF_2HCF_2Cl$ at equilibrium is significantly greater than 1.0 throughout the temperature range of 50° C. to 475° C., the invention is preferably employed for increasing the mole ratio of $CF_3CHClF$ to $CF_2HCF_2Cl$ in a composition.

HCFC-124 and HCFC-124a can be respectively converted to $CF_3CH_2F$ (HFC-134a) and $CF_2HCF_2H$ (HFC-134) by hydrogenolysis; and this invention provides a means for achieving desirable mixtures of HFC-134a and HFC-134.

A process is provided herein for producing a mixture of $CF_3CH_2F$ and $CF_2HCF_2H$ from a composition which comprises $CF_2HCF_2Cl$ and has an initial mole ratio of $CF_3CHClF$ to $CF_2HCF_2Cl$ less than the equilibrium mole ratio of $CF_3CHClF$ to $CF_2HCF_2Cl$ at 50° C. using hydrogenolysis. The process is characterized by increasing the mole ratio of $CF_3CH_2F$ to $CF_2HCF_2H$ in the product mixture produced from said composition by contacting said composition prior to said hydrogenolysis with a catalyst consisting essentially of a halided aluminum oxide, an aluminum halide, or mixtures thereof, for a time sufficient to allow the mole ratio of $CF_3CHFCl$ to $CF_2HCF_2Cl$ in said composition to increase by substantial interconversion between $CF_3CHFCl$ and $CF_2HCF_2Cl$; and providing during said catalyst contact, a temperature within the range of about 50° C. to 475° C. at which the equilibrium mole ratio of $CF_3CHFCl$ to $CF_2HCF_2Cl$ is greater than said initial mole ratio.

By controlling the hydrogenolysis so that the relative conversion of $CF_3CHFCl$ to $CF_3CH_2F$ and of $CF_2HCF_2Cl$ to $CF_2HCF_2H$ correspond, a process is provided herein for the preparation of a mixture of $CF_3CH_2F$ and $CF_2HCF_2H$ having a selected mole ratio of $CF_3CH_2F$ to $CF_2HCF_2H$ which is equal to or less than the equilibrium ratio of $CF_3CHFCl$ to $CF_2HCF_2Cl$ at 50° C., and includes the steps of: (1) providing a composition comprising $CF_2HCF_2Cl$ wherein the mole ratio of $CF_3CHClF$ to $CF_2HCF_2Cl$ in said composition is less than said selected mole ratio (e.g., by hydrogenolysis of $CClF_2CClF_2$); (2) contacting said composition with a catalyst consisting essentially of a halided aluminum oxide, an aluminum halide, or mixtures thereof, for a time sufficient to allow the mole ratio of $CF_3CHFCl$ to $CF_2HCF_2Cl$ in the composition to increase to said selected mole ratio or more by substantial interconversion between $CF_3CHFCl$ and $CF_2HCF_2Cl$; (3) providing during said catalyst contact, a temperature within the range of about 50° C. to 475° C. at which the equilibrium mole ratio of $CF_3CHFCl$ to $CF_2HCF_2Cl$ is at least equal to said selected mole ratio; (4) preparing a mixture of $CF_3CHFCl$ and $CF_2HCF_2Cl$ which comprises said catalyst-contacted composition and has a mole ratio of $CF_3CHFCl$ to $CF_2HCF_2Cl$ equal to said selected mole ratio; and (5) converting the $CF_3CHFCl$ and $CF_2HCF_2Cl$ in said mixture thereof respectively to $CF_3CH_2F$ and $CF_2HCF_2H$ by hydrogenolysis.

A process is also provided herein for producing a mixture of $CF_3CH_2F$ and $CF_2HCF_2H$ from a composition which comprises $CF_2HCF_2Cl$ and has an initial mole ratio of $CF_3CHClF$ to $CF_2HCF_2Cl$ greater than the equilibrium mole ratio of $CF_3CHClF$ to $CF_2HCF_2Cl$ at 475° C. using hydrogenolysis. This process is characterized by decreasing the mole ratio of $CF_3CH_2F$ to $CF_2HCF_2H$ in the product mixture produced from said composition by contacting said composition prior to said hydrogenolysis with a catalyst consisting essentially of a halided aluminum oxide, an aluminum halide, or mixtures thereof for a time sufficient to allow the mole ratio of $CF_3CHFCl$ to $CF_2HCF_2Cl$ in said composition to decrease by substantial interconversion between $CF_3CHFCl$ and $CF_2HCF_2Cl$; and providing during said catalyst contact, a temperature within the range of about 50° C. to 475° C. at which the equilibrium mole ratio of $CF_3CHFCl$ to $CF_2HCF_2Cl$ is less than said initial mole ratio.

By controlling the hydrogenolysis so that the relative conversion of $CF_3CHFCl$ to $CF_3CH_2F$ and of $CF_2HCF_2Cl$ to $CF_2HCF_2H$ correspond, a process for the preparation of a mixture of $CF_3CH_2F$ and $CF_2HCF_2H$ having a selected mole ratio of $CF_3CH_2F$ to $CF_2HCF_2H$ which is equal to or greater than the equilibrium ratio of $CF_3CHFCl$ to $CF_2HCF_2Cl$ at 475° C., is also provided herein and includes the steps of: (1) providing a composition comprising $CF_2HCF_2Cl$ wherein the mole ratio of $CF_3CHClF$ to $CF_2HCF_2Cl$ in said composition is greater than said selected mole ratio; (2) contacting said composition with a catalyst consisting essentially of a halided aluminum oxide, an aluminum halide, or mixtures thereof, for a time sufficient to allow the mole ratio of $CF_3CHFCl$ to $CF_2HCF_2Cl$ in the composition to decrease to said selected mole ratio or less by substantial interconversion between $CF_3CHFCl$ and $CF_2HCF_2Cl$; (3) providing during said catalyst contact, a temperature within the range of about 50° C. to 475° C. at which the equilibrium mole ratio of $CF_3CHFCl$ to $CF_2HCF_2Cl$ is at most equal to said selected mole ratio; (4) preparing a mixture of $CF_3CHFCl$ and $CF_2HCF_2Cl$ which comprises said catalyst-contacted composition and has a mole ratio of $CF_3CHFCl$ to $CF_2HCF_2Cl$ equal to said selected mole ratio; and (5) converting the $CF_3CHFCl$ and $CF_2HCF_2Cl$ in said mixture thereof respectively to $CF_3CH_2F$ and $CF_2HCF_2H$ by hydrogenolysis.

DETAILS OF THE INVENTION

The invention deals with processes for the interconversion of two chlorofluorohydrocarbons, $CF_3CHClF$ (HCFC-124) and $CClF_2CHF_2$ (HCFC-124a) using aluminum based catalysts, and with processes for preparing selected mixtures of HFC-134a and HFC-134.

Some processes which produce HCFC-124 (e.g., the gas phase fluorination of a suitable tetrahaloethylene described in U.S. Pat. No. 4,766,260) also produce varying amounts of its isomer HCFC-124a. These two compounds boil close to each other and cannot be conveniently separated by distillation. If the HCFC-124/HFC-124a mixture is hydrogenated, a mixture of HFC-134a/HFC-134 will be produced. The desirable proportion of HFC-134 to HFC-134 in HFC-134a/HFC-134 mixtures can vary according to the anticipated use. Other processes such as the hydrogenolysis of $CF_2ClCF_2Cl$ (CFC-114) produce HCFC-124a. This invention provides a means to vary the content of HCFC-124a so that hydrogenolysis provides a more desirable product.

The HCFC-124/HCFC-124a equilibrium is strongly temperature dependent. The lower the temperature, the lower the relative amount of HCFC-124a present at equilibrium. Equilibration processes always proceed in the direction of the equilibrium at the temperature used. To reduce HCFC-124a to as low a level as possible extremely active catalysts are needed because they must function at very low temperatures. To make additional HCFC-124a it is desirable to work at as high a temperature as possible. The catalyst need not have as high an activity, but it should not catalyze undesired levels of alternate reactions at the use temperature.

We have found that halided aluminum oxide and aluminum halides function as suitable catalysts for this reaction. Use of these catalysts can provide interconversion between HCFC-124a and HCFC-124 without substantial loss of $C_2HClF4$ due to disproportionation. For example, total loss of $C_2HClF4$ isomers can generally be held below 5% during interconversion using a catalyst consisting essentially of a halided aluminum oxide, an aluminum halide, or mixtures thereof. Accordingly, the wherein the mole ratio is less than the equilibrium mole ratio at 50° C. can be increased by contacting the composition with a catalyst of halided aluminum oxide and/or aluminum halides for a time sufficient to provide substantial interconversion between $CF_3CHClF$ and $CClF_2CHF_2$, and providing during said catalyst contact a temperature within the range of about 50° C. to 475° C. at which the mole ratio of $CF_3CHClF$ to $CClF_2CHF_2$ increases. The mole ratio of $CClF_2CHF_2$ to $CF_3CHClF$ in a composition wherein the mole ratio is less than the equilibrium mole ratio at 475° C. can be increased by contacting the mixture with a catalyst of halided aluminum oxide and/or aluminum halides for a time sufficient to provide substantial interconversion between $CF_3CHClF$ and $CClF_2CHF_2$, and providing during said catalyst contact a temperature within the range of about 50° C. to 475° C. at which the mole ratio of $CClF_2CHF_2$ to $CF_3CHClF$ increases. For practical reasons, the liquid phase reaction is typically conducted at a temperature within the range of about 50° C. to about 130° C. (i.e., below the critical temperatures of HCFC-124 and HCFC-124a); and liquid mixtures wherein the mole ratio of $CClF_2CHF_2$ to $CF_3CHClF$ is to be increased, preferably have a mole ratio of $CClF_2CHF_2$ to $CF_3CHClF$ which is less than the equilibrium mole ratio at about 130° C. Halided aluminum oxides are most useful in a vapor phase process. Aluminum halides are more useful in a liquid phase process.

By halided aluminum oxide is meant a material comprising aluminum, oxygen, and a halogen, the halogen being either chlorine or fluorine. The halogen content can vary from 1% with either halogen to nearly 70% if the halogen is fluorine. The remainder of the material may include alumina, aluminum oxyfluoride, and aluminum oxychloride.

Catalysts based on fluorided alumina can be prepared prior to reaction with HCFC-124a by treatment with a vaporizable fluorine-containing fluorinating compound, such as HF, CCl3F (CFC-11), $CCl_2F_2$ (CFC-12), $CHF_3$, or $CCl_2FCClF_2$ (CFC-113), at elevated temperatures until the desired degree of fluorination is obtained, e.g., at about 200° C. to 450° C. By vaporizable fluorine-containing compound is meant a compound which will convert the alumina component of the instant invention to the desired degree of fluorination using the pretreatment conditions described herein. Such treatments are well known to the art.

Catalysts based on chlorided alumina can be prepared by treatment with a vaporizable chlorocarbon such as $Cl_4$ or $C_2Cl_4$. The treatments can conveniently be done in the reactor which is to be used for equilibrating HCFC-124a and HCFC-124.

A suitable catalyst may be prepared as follows:

A quantity of alumina ($Al_2O_3$) is dried until essentially all moisture is removed, e.g., for about 18 hours at 100° C. The dried catalyst is then transferred to the reactor to be used. The temperature is then gradually increased to about 400° C. while maintaining a flow of $N_2$ through the reactor to remove any remaining traces of moisture from the catalyst and the reactor. The temperature is then lowered to about 200° C., and CFC-12 in $N_2$ is passed through the reactor. The $N_2$ can be gradually reduced until only CFC-12 is being passed through the reactor. At this point the temperature can be increased to about 350° C. and held at that temperature to convert the $Al_2O_3$ to the desired halide content. If too much chlorine containing activator is used, some aluminum may be lost as $AlCl_3$. If too little is used, further activation will occur when the HCFC-124a feed is started.

If the purpose of the process is to reduce the content of HCFC-124a relative to HCFC-124, the reaction should be run at lower temperatures, preferably below 100° C. The tradeoff is a lower content of HCFC-124a at equilibrium at the lower temperature, but at the expense of a longer contact time. If the purpose of the process is to produce HCFC-124a from HCFC-124, then the reaction should be run at higher temperatures and shorter contact times. The liquid phase interconversion between HCFC-124a and HCFC-124 can be conducted between 50° C. and about 130° C. The same logic determines the appropriate temperature in both the liquid and vapor phase processes. Because the molar ratio of HCFC-124 to HCFC-124a at equilibrium is significantly greater than 1.0 throughout the temperature range of 50° C. to 475° C., the invention is especially useful for increasing the mole ratio of HCFC-124 to HCFC-124a in a composition. For example, mixtures having mole ratio of $CF_3CHFCl$ to $CF_2HCF_2Cl$ above about 10:1 can be prepared from compositions wherein the mole ratio thereof is below about 0.5:1.

Compositions for catalytic treatment in accordance with this invention may comprise $CF_3CHClF$ and $CClF_2CHF_2$. If the ratio of $CF_3CFHCl$ to $CF_2ClCF_2H$ is to be increased, the mole ratio of $CF_3CHClF$ to $CClF_2CHF_2$ prior to catalyst contact should be less than the equilibrium ratio of $CF_3CHClF$ to $CClF_2CHF_2$ at 50° C. If the ratio of $CF_2ClCF_2H$ to $CF_3CHClF$ is to be increased, the mole ratio of $CF_2ClCF_2H$ to $CF_3CHClF$ prior to catalyst contact should be less than the equilibrium ratio of $CF_2ClCF_2H$ to $CF_3CHClF$ at 475° C. Thus, depending upon the isomer selected, mixtures of HCFC-124 and HCFC-124a in any proportion may be used as feed to the reactor.

A gas phase process is provided in accordance with this invention, for increasing in a composition the mole ratio of one compound selected from the group consisting of $CF_3CHClF$ and $CClF_2CHF_2$ relative to the other compound of said group. A particular gas phase process provided by this invention comprises the steps of: (a) providing a gaseous composition comprising at least one compound of said group provided that (i) if the selected compound is $CF_3CHClF$, the mole ratio of $CF_3CHClF$ to $CClF_2CHF_2$ in said gaseous composition is less than the equilibrium ratio thereof at 50° C., and (ii) if the selected compound is $CClF_2CHF_2$, the mole ratio of $CClF_2CHF_2$ to $CF_3CHClF$ in said gaseous composition is less than the equilibrium ratio thereof at 475° C.; (b) contacting said gaseous composition with a catalyst consisting essentially of a halided aluminum oxide, an aluminum halide or mixtures thereof, for a time sufficient to provide substantial interconversion between $CF_3CHClF$ and $CClF_2CHF_2$; and (c) providing during said catalyst contact a temperature within the range of about 50° C. to 475° C. at which the mole ratio of the selected compound to the other compound increases.

The contact time in the vapor phase process can vary widely depending on the degree of conversion desired and generally will be about 1 to 1000 seconds, preferably about 10 to 60 seconds.

The chlorofluoroethane isomers (HCFC-124 and HCFC-124a) may be fed to a vapor phase process as is or diluted with an inert gas such as nitrogen, helium or argon. Small amounts of other chlorofluorohydrocarbons (HCFCs), that is, compounds containing only chlorine, hydrogen, fluorine and carbon; chlorofluorocarbons (CFCs), that is, compounds containing only fluorine, chlorine and carbon; and fluorohydrocarbons (HFCs), that is, compounds containing fluorine, hydrogen and carbon; do not interfere with the HCFC- 124/HCFC-124a equilibration if they do not differ greatly from HCFC-124 in the ratios of halogens present.

A liquid phase process is also provided in accordance with this invention for increasing in a composition the ratio of one compound selected from the group consisting of $CF_3CFClF$ and $CClF_2CHFz$ relative to the other compound of said group. A particular liquid phase process provided by this invention comprises the steps of: (a) providing a liquid composition comprising at least one compound of said group provided that (i) if the selected compound is $CF_3CHClF$, the mole ratio of $CF_3CHClF$ to $CClF_2CHF_2$ in said liquid composition is less than the equilibrium ratio thereof at 50° C., and (ii) if the selected compound is $CClF_2CHF_2$, the mole ratio of $CClF_2CHF_2$ to $CF_3CHClF$ in said liquid composition is less than the equilibrium ratio thereof at about 130° C.; (b) contacting said liquid composition with a catalyst consisting essentially of a halided aluminum oxide, an aluminum halide or mixtures thereof, for a time sufficient to provide substantial interconversion between $CF_3CHClF$ and $CClF_2CHF_2$; and (c) providing during said catalyst contact a temperature within the range of about 50° C. to about 130° C. at which the mole ratio of the selected compound to the other compound increases.

The contact time in the liquid phase process can vary widely depending on the degree of conversion desired and generally will be about 0.1 to 8 hours, preferably about 0.5 to 2 hours.

The chlorofluoroethane isomers in the liquid process may be neat or mixed with an inert liquid such as $CF_3Cl_3$ (CFC-113a) or $Cl_4$.

The vapor phase interconversion of HCFC-124a and HCFC-124 may be conducted in any suitable reactor, including fixed and fluidized bed reactors. The liquid phase reaction likewise may be carried out in many types of reactors including batch autoclaves or continuous slurry reactors. It is important to minimize water content in the liquid phase processes. The reaction vessel should be constructed from materials which are resistant to the corrosive effects of hydrogen halides, such as Hastelloy ® nickel alloy and Inconel ® nickel alloy.

Pressure is not critical. Atmospheric and superatmospheric pressures are the most convenient and are therefore preferred.

Compositions comprising both $CF_3CHClF$ and $CClF_2CHF_2$ may be provided as a product (e.g., a reaction product) containing both compounds. Alternatively, either HCFC-124 or HCFC-124a may be provided. It will be evident that even where HCFC-124 is initially provided without HCFC-124a or where HCFC-124a is initially provided without HCFC-124 even partial equilibration will produce a quantity of the compound not initially provided. Accordingly, mixtures comprising both compounds may be treated in accordance with step (a).

HCFC-124 and HCFC-124a are both useful as refrigerants and as chemical intermediates for producing other refrigerants.

A process is provided herein for producing a mixture of $CF_3CH_2F$ and $CF_2HCF_2H$ from a composition which comprises $CF_2HCF_2Cl$ and has an initial mole ratio of $CF_3CHClF$ to $CF_2HCF_2Cl$ less than the equilibrium mole ratio of $CF_3CHClF$ to $CF_2HCF_2Cl$ at 50° C. using hydrogenolysis. The process is characterized by increasing the mole ratio of $CF_3CH_2F$ to $CF_2HCF_2H$ in the product mixture produced from said composition by contacting said composition prior to said hydrogenolysis with a catalyst consisting essentially of a halided aluminum oxide, an aluminum halide, or mixtures thereof, for a time sufficient to allow the mole ratio of $CF_3CHFCl$ to $CF_2HCF_2Cl$ in said composition to increase by substantial interconversion between $CF_3CHFCl$ and $CF_2HCF_2Cl$; and providing during said catalyst contact, a temperature within the range of about 50° C. to 475° C. at which the equilibrium mole ratio of $CF_3CHFCl$ to $CF_2HCF_2Cl$ is greater than said initial mole ratio.

Hydrogenolysis of the composition comprising $CF_3CHFCl$ and $CF_2HCF_2Cl$ to produce a mixture of $CF_3CH_2F$ and $CF_2HCF_2H$ may be accomplished, for example, by reacting the $CF_3CHFCl$ and $CF_2HCF_2Cl$ with hydrogen at temperatures between about 200° C. and 450° C. in the presence of a conventional catalyst such as palladium supported on carbon or palladium supported on alumina. Alternatively the use of precious metals can be avoided by reacting the $CF_3CHFCl$ and $CF_2HCF_2Cl$ with hydrogen at a temperature between about 350° C. and 700° C. in a reaction vessel of nickel, iron, cobalt or their alloys which either is empty or is packed with silica, silicon carbide, or low surface area carbon, or with nickel, iron, cobalt or their alloys (e.g., as metal pipe, screen, wool, gauze, wire, chips or shot). Reference is made to U.S. Patent application Ser. No. 07/418,832 for further discussion of such high temperature processes.

Where the hydrogenolysis is controlled so that the relative conversions of $CF_3CHFCl$ to $CF_3CH_2F$ and of $CF_2HCF_2Cl$ to $CF_2HCF_2H$ correspond, the interconversion of this invention can be used to obtain a tetrafluoroethane product having a selected mole ratio of $CF_3CH_2F$ to $CF_2HCF_2H$. Accordingly, the present invention also provides a process for the preparation of a mixture of $CF_3CH_2F$ and $CF_2HCF_2H$ having a selected mole ratio of $CF_3CH_2F$ to $CF_2HCF_2H$ which is equal to or less than the equilibrium ratio of $CF_3CHFCl$ to $CF_2HCF_2Cl$ at 50° C., said process including the steps of: providing a composition comprising $CF_2HCF_2Cl$ wherein the mole ratio of $CF_3CHClF$ to $CF_2HCF_2Cl$ in said composition is less than said selected mole ratio; contacting said composition with a catalyst consisting essentially of a halided aluminum oxide, an aluminum halide, or mixtures thereof, for a time sufficient to allow the mole ratio of $CF_3CHFCl$ to $CF_2HCF_2Cl$ in the composition to increase to said selected mole ratio or more by substantial interconversion between $CF_3CHFCl$ and $CF_2HCF_2Cl$; providing during said catalyst contact, a temperature within the range of about 50° C. to 475° C. at which the equilibrium mole ratio of $CF_3CHFCl$ to $CF_2HCF_2Cl$ is at least equal to said selected mole ratio; preparing a mixture of $CF_3CHFCl$ and $CF_2HCF_2Cl$ which comprises said catalyst{contacted composition and has a mole ratio of $CF_3CHFCl$ to $CF_2HCF_2Cl$ equal to said selected mole ratio; and converting the $CF_3CHFCl$ and $CF_2HCF_2Cl$ in said mixture thereof respectively to $CF_3CH_2F$ and $CF_2HCF_2H$ by hydrogenolysis.

The catalyst contact of this process may be controlled so that the resulting composition is a mixture of $CF_3CHFCl$ to $CF_2HCF_2Cl$ equal to the selected ratio. For example, to achieve a composition having a desired mole ratio of HCFC-124 to HCFC-124a of about 19:1 from a starting composition wherein the mole ratio of HCFC-124 to HCFC-124a is about 1:9, one can control contact with the catalyst (e.g., contact the starting composition with fluorinated alumina catalyst at, say, 250° C.) until the desired ratio is reached. Alternatively, the composition resulting from catalyst contact can have a mole ratio of $CF_3CHFCl$ to $CF_2HCF_2Cl$ which is greater than the selected mole ratio, and the mixture of $CF_3CHFl$ and $CF_2HCF_2Cl$ having the selected mole ratio can be prepared by mixing the catalyst-contacted composition with another composition having relatively higher levels of $CF_2HCF_2Cl$ (e.g., additional amounts of the composition which is used for catalyst contact). For example, to achieve a composition having a desired mole ratio of HCFC-124 to HCFC-124a of about 19:1 from a starting composition wherein the mole ratio of HCFC-124 to HCFC-124a is about 1:9, one can contact the starting composition with the catalyst under conditions where the ratio of HCFC-124 to HCFC-124a reaches about 99:1 and then mix said catalyst-contacted composition with additional amounts of starting composition which are sufficient to adjust the resulting ratio of HCFC-124 to HCFC-124a in the mixture to the desired 19:1.

This invention is especially useful for preparing mixtures wherein the mole ratio of $CF_3CH_2F$ to $CF_2HCF_2H$ is above about 10:1 from compositions wherein the initial mole ratio of $CF_3CHFCl$ to $CF_2HCF_2Cl$ is below about 0.5:1. The composition contacted with the catalyst of halided aluminum oxide and/or aluminum halide in this process can be provided as a reaction product. The product of hydrogenolysis of $CF_2ClCF_2Cl$ is noted as a source of compositions where the mole ratio of $CF_3CHFCl$ to $CF_2HCF_2Cl$ is low. Thus, for example, the step of providing a composition comprising $CF_2HCF_2Cl$ wherein the mole ratio of $CF_2CHClF$ to $CF_2HCF_2Cl$ is less than the selected mole ratio may be accomplished by hydrogenolysis of $CF_2ClCF_2Cl$.

Hydrogenolysis of $CF_2ClCF_2Cl$, for example, may be accomplished by reacting it with hydrogen at temperatures between about 200° C. and 450° C. in the presence of a conventional catalyst such as palladium supported on carbon or palladium supported on alumina. Alternately, the use of precious metal catalysts can be avoided by reacting $CF_2ClCF_2Cl$ with hydrogen at a temperature between about 350° C. and 700° C. in a reactor vessel of nickel, iron, cobalt or their alloys which either is empty or is packed with silica, silicon carbide, or low surface area carbon, or with nickel, iron, cobalt or their alloys (e.g., as metal pipe, screen, wool, gauze, wire, chips or shot). Reference is made to copending U.S. Patent Application Serial No. 07/418,832 for further discussion of such high temperature processes.

Other starting compositions comprising $CF_2HCF_2Cl$ can be derived (either directly or by partial equilibration) from reaction products obtained by reacting suitable tetrahaloethylenes (e.g., $CCl_2=CCl_2$) or pentahaloethanes with HF in the presence of suitable catalysts as exemplified by U.S. Pat. No. 4,766,260 and 4,843,181.

A process is also provided herein for producing a mixture of $CF_3CH_2F$ and $CF_2HCF_2H$ from a composition which comprises $CF_2HCF_2Cl$ and has an initial mole ratio of $CF_3CHClF$ to $CF_2HCF_2Cl$ greater than the equilibrium mole ratio of $CF_3CHClF$ to $CF_2HCF_2Cl$ at 475° C. using hydrogenolysis. This process is characterized by decreasing the mole ratio of $CF_3CH_2F$ to $CF_2HCF_2H$ in the product mixture produced from said composition by contacting said composition prior to said hydrogenolysis with a catalyst consisting essentially of a halided aluminum oxide, an aluminum halide, or mixtures thereof for a time sufficient to allow the mole ratio of $CF_3CHFCl$ to $CF_2HCF_2Cl$ in said composition to decrease by substantial interconversion between $CF_3CHFCl$ and $CF_2HCF_2Cl$; and providing during said catalyst contact, a temperature within the range of about 50° C. to 475° C. at which the equilibrium mole ratio of $CF_3CHFCl$ to $CF_2HCF_2Cl$ is less than said initial mole ratio.

It is preferred that for liquid phase interconversion the initial ratio of $CF_3CHClF$ to $CF_2HCF_2Cl$ is greater than the equilibrium ratio thereof at about 130° C.; and that for liquid phase conversion the temperature provided during catalyst contact is within the range of about 50° C. to about 130° C.

Where the hydrogenolysis is controlled so that the relative conversions of $CF_3CHFCl$ to $CF_3CH_2F$ and of $CF_2HCF_2Cl$ to $CF_2HCF_2H$ correspond, the present invention further provides a process for the preparation of a mixture of $CF_3CH_2F$ and $CF_2HCF_2H$ having a selected mole ratio of $CF_3CH_2F$ to $CF_2HCF_2H$ which is equal to or greater than the equilibrium ratio of $CF_3CHFCl$ to $CF_2HCF_2Cl$ at 475° C., said process including the steps of: providing a composition comprising $CF_2HCF_2Cl$ wherein the mole ratio of $CF_3CHClF$ to $CF_2HCF_2Cl$ in said composition is greater than said selected mole ratio; contacting said composition with a catalyst consisting essentially of a halided aluminum oxide, an aluminum halide, or mixtures thereof, for a time sufficient to allow the mole ratio of $CF_3CHFCl$ to $CF_2HCF_2Cl$ in the composition to decrease to said selected mole ratio or less by substantial interconversion between $CF_3CHFCl$ and $CF_2HCF_2Cl$; providing during said catalyst contact, a temperature within the range of about 50° C. to 475° C. at which the equilibrium mole ratio of $CF_3CHFCl$ to $CF_2HCF_2Cl$ is at most equal to said selected mole ratio; preparing a mixture of $CF_3CHFCl$ and $CF_2HCF_2Cl$ which comprises said catalyst-contacted composition and has a mole ratio of $CF_3CHFCl$ to $CF_2HCF_2Cl$ equal to said selected mole ratio; and converting the $CF_3CHFCl$ and $CF_2HCF_2Cl$ in said mixture thereof respectively to $CF_3CH_2F$ and $CF_2HCF_2H$ by hydrogenolysis.

It is preferred that liquid phase interconversion to decrease the mole ratio of $CF_3CHFCl$ to $CF_2HCF_2Cl$ be employed in this process only when the selected mole ratio of $CF_3CH_2F$ to $CF_2HCF_2H$ is equal to or greater than the equilibrium ratio of $CF_3CHFCl$ to $CF_2HCF_2Cl$ at about 130° C.; and that for liquid phase conversion the temperature provided during catalyst contact be within the range of about 50° C. to about 130° C.

The catalyst contact of this process may be controlled so that the resulting composition is a mixture of $CF_3CHFCl$ and $CF_2HCF_2Cl$ which has a mole ratio of $CF_3CHFCl$ to $CF_2HCF_2Cl$ equal to the selected ratio. For example, to achieve a composition having a desired mole ratio of HCFC-124 to HCFC-124a of about 49:1 from a starting composition wherein the mole ratio is about 199:1, one can control contact of HCFC-124 to HCFC-124a with the catalyst (e.g., contact the starting composition with fluorinated alumina catalyst at, say, 450° C.) until the desired ratio is reached. Alternatively, the composition resulting from catalyst contact can have a mole ratio of $CF_3CHFCl$ to $CF_2HCF_2Cl$ which is greater than the selected mole ratio, and the mixture of $CF_3CHFCl$ and $CF_2HCF_2Cl$ having the selected mole ratio can be prepared by mixing the catalyst-contacted composition with another composition having relatively lower levels of $CF_2HCF_2Cl$ (e.g., additional amounts of the composition which is used for catalyst contact). For example, to achieve a composition having a desired mole ratio of HCFC-124 to HCFC-124a of about 49:1 from a starting composition wherein the mole ratio of HCFC-124 to HCFC-124a is about 199:1, one can contact the starting composition with the catalyst until the ratio of HCFC-124 to HCFC-124a reaches about 24:1 and then mix said catalyst-contacted composition with additional amounts of starting composition which are sufficient to adjust the resulting ratio of HCFC-124 to HCFC-124a in the mixture to the desired 49:1.

HFC-134 and HFC-134a are useful as refrigerants.

Practice of the invention will be made further apparent from the following non-limiting examples.

EXAMPLES

In the following illustrative Examples, all parts and percentages are by weight and all temperatures are Celsius. All product compositions are area percent.

General Procedure for Vapor Phase Equilibration

The catalyst was pretreated by heating first with $N_2$ with a chlorofluorocarbon, hydrochlorofluorocarbon, hydrofluorocarbon, HF, or HCl to replace some oxygen of the alumina with halogen. After pretreatment the temperature was adjusted to the indicated values with a flow of $N_2$. When the proper temperature was reached the chlorofluoroethane flow and an inert gas (if used) was started. The reactor was given time to come to steady state and the effluent sampled on-line and optionally a liquid sample collected at $-78°$ C. for further analyses.

General Procedure for Liquid Phase Equilibration

Catalyst was loaded into a 10 cc Hastelloy ® B nickel alloy shaker tube. The tube was cooled to $-78°$ C. and evacuated. The desired amount of chlorofluoroethane was transferred into the tube. The sealed tube was placed in a shaker in a barricade and heated at the indicated temperatures and times. At the end of the reaction of tube was again cooled to $-78°$ C. and the contents removed. The liquid was analyzed using the same GC conditions as for the vapor phase experiments.

Gas Chromatographic Conditions

The reactor effluent was analyzed using a Varian 6000 gas chromatograph equipped with a 10 foot×⅛ inch OD column containing Krytox ® perfluorinated polyether on an inert support and a helium flow of 20 cc/minute. The temperature program was 70° C. for 6.5 minutes with a ramp to 180° C. at a rate of 35° C./minute. Compounds were monitored by measuring peaks in area percent using a thermal conductivity detecter (TCD).

EXAMPLE 1

The reactor was loaded with 10.7 g $Al_2O_3$, and activated at 350° C. with CFC-12 (@ 5 mL/minute). A feed was then provided at about 3 mL/minute. The ratio results at various temperatures are shown in Table 1.

TABLE 1

| Temp. | 124/124a* |
|---|---|
| Start | 18 |
| 102 | 960 |
| 85 | 1600 |
| 70 | 2400 |
| 62 | 3250 |
| 52 | 4900 |
| 46 | 9800 |

*124/124a = $CF_3CHClF/CHF_2CClF_2$ area percent ratio

This example shows the effect of changing temperature, and exemplifies a method for maximizing HCFC-124 by a vapor phase process.

EXAMPLE 2

The reactor was loaded with 4 g $Al_2O_3$ and activated with $CCl_4$. Table 2 records the HCFC-124/HCFC-124a ratio as a function of temperature with a flow rate of HCFC-124a of 5 mL/minute. Under these conditions trace amounts of CFC-114 were also detected in the product.

TABLE 2

| Temp. | 124/124a |
|---|---|
| 350 | 0.10 |
| 400 | 1.3 |
| 450 | 10.9 |

This example demonstrates starting with pure HCFC-124a.

EXAMPLE 3

The reactor was loaded with 4.7 g $Al_2O_3$ and activated at 350° C. with CFC-12 for .5 hr. A feed was then provided at about 3 mL/minute. The ratio results at various temperatures are shown in Table 3.

TABLE 3

| Temp. | 124/124a |
|---|---|
| start | 150 |
| 149 | 450 |
| 175 | 230 |
| 197 | 140 |
| 225 | 90 |
| 251 | 61 |
| 275 | 46 |
| 300 | 47 |
| 328 | 47 |
| 349 | 37 |
| 376 | 26 |
| 401 | 16 |

This example demonstrates that the mole ratio can be adjusted in either direction, dependent on temperature, when starting from low HCFC-124a compositions.

EXAMPLE 4

Table 4 presents the results of heating in a shaker tube 2 g HCFC-124 containing 5.5% HCFC-124a with $AlCl_3$.

TABLE 4

| Temp. °C. | Time hour | $AlCl_3$ Wt. (g) | 124/124a | 123*/124 | $C_2Cl_4$ |
|---|---|---|---|---|---|
| 150 | 4 | 0.05 | 3040 | ND | 0.056 |
| 150 | 1 | 0.05 | 2860 | ND | 0 |
| 250 | 1 | 0.5 | 38 | 0.69 | 0 |
| 100 | 2 | 0.5 | 3300 | 0.14 | 0 |

TABLE 4-continued

| Temp. °C. | Time hour | AlCl$_3$ Wt. (g) | 124/124a | 123*/124 | C$_2$Cl$_4$ |
|---|---|---|---|---|---|
| 100 | 2 | 0.15 | 75 | 3 × 10$^{-4}$ | 0 |

*123 = CF$_3$CHCl$_2$

This example demonstrates the liquid phase process with AlCl$_3$.

EXAMPLE 5

Preparation of CFC-11 modified AlCl$_3$

Anhydrous, powdered AlCl$_3$ (50 g) was placed in a N$_2$ flushed 500 mL flask equipped with thermometer, addition funnel, reflux condenser, and mechanical stirrer. The solid was cooled with a room temperature acetone bath and 175 mL of CFCl$_3$ (CFC-11) was added dropwise over a 15 minute period. The suspension was stirred an additional two hours. Liquid was removed under reduced pressure giving 37 g of CFC-11 modified AlCl$_3$.

Table 5 presents the results of heating 2 g HCFC-124 containing 5.5% HCFC-124a with this modified AlCl$_3$.

TABLE 5

| Temp. °C. | Time hour | Mod-AlCl$_3$ Wt. (g) | 124/124a | 123/124 | C$_2$Cl$_4$ |
|---|---|---|---|---|---|
| start | — | — | 18 | 0 | 0 |
| 100 | 2 | 0.5 | 2290 | 0.21 | 0.09 |
| 100 | 2 | 0.05 | 1370 | 0.01 | 0.001 |
| 75 | 2 | 0.05 | 1020 | 0.04 | 0.5 × 10$^{-4}$ |

This example demonstrates the liquid phase process with F-modified AlCl$_3$. These runs have much less HCFC-123 and C$_2$Cl$_4$ than vapor phase runs at the same temperature.

COMPARATIVE EXAMPLE 6

The reactor was loaded with 10 g Al$_2$O$_3$ and activated for 5 hours with CFC-12 (@ 20 mL/minute). A feed of 2% mL/hour. Results, including 122/122a ratios at various temperatures are shown in Table 6.

TABLE 6

| Temp.°C. | 122/122a | 1111/122 |
|---|---|---|
| start | 52 | 0 |
| 294 | 550 | 0.88 |
| 249 | 310 | 0.13 |
| 207 | 100 | 0.02 |
| 188 | 66 | — |

This example shows the results of using the most preferred catalyst to isomerize CClF$_2$CHCl$_2$ (HCFC-122) and CCl$_2$FCHClF (HCFC-122a). The olefin CCl$_2$=CClF (CFC-1111) is a major by-product. Olefins are much less significant in a HCFC-124 system.

COMPARATIVE EXAMPLE 7

The reactor was loaded with 5 g Cr$_2$O$_3$ (no pretreatment). The feed was then provided at about 7 mL/minute. Results are shown in Table 7.

TABLE 7

| Temp. °C. | 124/124a | 125/124 | 123/124 |
|---|---|---|---|
| start | 18 | | |
| 120 | 24 | <0.1 | <0.1 |
| 140 | 224 | <0.1 | 0.1 |
| 175 | 196 | 0.2 | 0.4 |

TABLE 7-continued

| Temp. °C. | 124/124a | 125/124 | 123/124 |
|---|---|---|---|
| 218 | 142 | 0.3 | 0.7 |
| 238 | 125 | 0.6 | 1.3 |
| 256 | 116 | 0.7 | 1.5 |
| 258 | 127 | 0.8 | 1.8 |
| 258 | 119 | 1.6 | 2.1 |
| 277 | 95 | 1.6 | 1.9 |
| 277 | 79 | 1.8 | 2.1 |
| 307 | 72 | 2.5 | 1.6 |

This comparative example shows the results of using a Cr$_2$O$_3$ catalyst. This catalyst also disproportionates the HCFC-124a to HCFC-123 and CF$_3$CHF$_2$ (HCFC-125)

COMPARATIVE EXAMPLE 8

HCFC-124a (~5mL/minute) and H$_2$ (5 mL/minute) were fed to 4 g 0.5% Pd/Al$_2$O$_3$ at 400° C. The effluent contained (relative area using a TCD) 7 HFC-134a, 67 HCF-134, 1000 HCFC-124a, 120 HCFC-124, and 375 CFC-114.

This example shows that isomerization and hydrogenation can take place simultaneously in the presence of a Pd/Al$_2$O$_3$ catalyst.

EXAMPLE 9

HCFC-124a→HCFC-124

A. Catalyst Preparation-Alumina (10.9 g of 1/16" extrudate) was placed in a ⅜"×8" Hastelloy ® C nickel alloy tube wrapped with heating tape. Diochlorodifluoromethane was passed over the alumina at 10 cc/minute, at 225° C. for four hours before use in the isomerization reaction.

B. HCFC-124a containing about 6% (by area) HCFC-124a was fed to a vaporizer at 2 mL/hour and then passed at atmospheric pressure through the catalyst contained in the apparatus as described in A at 120° C. The average HCFC-124a content of the effluent was 0.29%, a 20-fold reduction. Traces of CF$_3$CHCl$_2$ and CF$_3$CClF$_2$ were also observed.

EXAMPLE 10

HCFC-124/HCFC-124a+H$_2$→HFC-134

The isomerizer effluent (Example 9B) was passed through an empty 156"×15" Hastelloy ® nickel alloy tube heated in a fluidized sand bath at 2 mL/hour together with hydrogen (molar ratio of hydrogen to the HCFC-124 isomer mixture was 1) at 550° C. and 1 atm. Over a four-hour period the organic content of the reactor effluent averaged 98.3% HFC-134a and 1.7% HFC-134.

COMPARATIVE EXAMPLE 11

HCFC-124a Isomerization

A 0.5" ID×12" long Inconel ® nickel alloy pipe was charged with 2% CoCl$_2$Al$_2$O$_3$ (20.4 g, 30 mL). The bath was gradually heated to 176° C. while nitrogen gas at a flow rate of 50 cc/minute was passed through the reactor to remove traces of water. The N$_2$HF flow was continued at a bath temperature of 176° C. for four hours. The HF flow was then stopped and only N$_2$ was passed over the catalyst overnight at 176° C. The HF flow was started again the next day. After 10 minutes the HF flow was increased to 75 cc/minute and the N$_2$ flow decreased to 25 cc/minute. The bath temperature was then increased to 263° C. at the higher HF flow rate and maintained under those conditions for 1.3 hours followed by the following heating profile: 281° C. for 13 minutes; 313° C. for 22 minutes; 352° C. for 15 minutes; and finally at 399° C. for 15 minutes. The HF flow was then stopped and the temperature of the bath reduced to reaction temperature. The results of passing HCFC-124a over the activated catalyst at a contact time of 30 seconds is shown in the table. The reactor effluent was analyzed with a Hewlett Packard HP 5890 gas chromatograph using a 20 foot long, ⅛" diameter, column containing Krytox® perfluorinated polyether on an inert support and a helium flow of 35 cc/minute. Gas chromatographic conditions were 70° C. for 3 minutes followed by temperature programming to 180° C. at a rate of 6° C./minute. Results at various temperatures are shown below.

| Temp. | $N_2$/124a | % F125 | % F124a | % F124 | % F123a | % F123 | % F114 |
|---|---|---|---|---|---|---|---|
| start | 3/1 | 0.0 | 87.1 | 1.9 | 0.0 | 0.0 | 8.7 |
| 250° C. | 1/1 | 34 | 33 | 4 | 0.2 | 7 | 9 |
| 300° C. | 1/1 | 48 | 3 | 10 | 0.1 | 16 | 8 |
| 350° C. | 1/1 | 45 | 0.4 | 15 | 0.1 | 15 | 6 |
| 125° C. | 0/1 | 3 | 82 | 2 | 0 | 0 | 10 |
| 225° C. | 0/1 | 34 | 33 | 3 | 0.2 | 7 | 10 |

Particular embodiments of the invention are included in the Examples. Other embodiments of the invention will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the claims.

What is claimed is:

1. A process for producing a mixture of $Cf_3CH_2F$ and $CF_2HCF_2H$ from a composition which comprises $CF_2HCF_2Cl$ and has an initial mole ratio of $CF_2CHClF$ to $CF_2HCF_2Cl$ less than the equilibrium mole ratio of $CF_3CHClF$ to $CH_2HCF_2Cl$ at 50° C. using hydrogenolysis, characterized by increasing the mole ratio of $CF_3CH_2F$ to $CF_2HCF_2H$ in the product mixture produced from said composition by contacting said composition prior to said hydrogenolysis with a catalyst consisting essentially of a halided aluminum oxide, an aluminum halide, or mixtures thereof, for a time sufficient to allow the mole ratio of $CF_3CHFCl$ to $CF_2HCF_2Cl$ in said composition to increase by substantial interconversion between $DV_2CHFCl$ and $CF_2HCF_2Cl$; and providing during said catalyst contact, a temperature within the range of about 50° C. to 475° C. at which the equilibrium mole ratio of $CF_3CHFCl$ to $CF_2HCF_2Cl$ is greater than said initial mole ratio.

2. A process in accordance with claim 1 for the preparation of a mixture of $CF_3CH_2F$ and $CF_2HCF_2H$ having a selected mole ratio of $CF_3CH_2F$ to $CF_2HCF_2H$ which is equal to or less than the equilibrium ratio of $CF_3CHFCl$ to $CF_2HCF_2Cl$ at 50° C., including the steps of:
   (1) providing a composition comprising $CF_2HCF_2Cl$ wherein the mole ratio of $CF_3CHClF$ to $CF_2HCF_2Cl$ in said composition is less than said selected mole ratio;
   (2) contacting said composition with a catalyst consisting essentially of a halided aluminum oxide, an aluminum halide, or mixtures thereof, for a time sufficient to allow the mole ratio of $CF_3CHFCl$ to $CF_2HCF_2Cl$ in the composition to increase to said selected mole ratio or more by substantial interconversion between $CF_2CHFCl$ and $CF_2HCF_2Cl$;
   (3) providing during said catalyst contact, a temperature within the range of about 50° C. to 475° C. at which the equilibrium mole ratio of $CF_3CHFCl$ to $CF_2HCF_2Cl$ is at least equal to said selected mole ratio;
   (4) preparing a mixture of $CF_3CHFCl$ and $CF_2HCF_2Cl$ which comprises said catalyst-contacted composition and has a mole ratio of $CF_3CHFCl$ to $CF_2HCF_2Cl$ equal to said selected mole ratio; and
   (5) converting the $CF_3CHFCl$ and $CF_2HCF_2Cl$ in said mixture thereof respectively to $CF_3CH_2F$ and $CF_2HCF_2H$ by hydrogenolysis.

3. The process of claim 1 wherein catalyst contact is accomplished in the liquid phase; wherein the catalyst is an aluminum halide; and wherein the temperature provided during catalyst contact is within the range of about 50° C. to about 130° C.

4. The process of claim 1 wherein catalyst contact is accomplished in the gas phase; and wherein the catalyst is a halided aluminum oxide.

5. The process of claim 1 wherein mixtures having a mole ratio of $CF_3CH_2F$ to $CF_2HCF_2H$ above about 10:1 are prepared from starting compositions wherein the mole ratio of $CF_3CHFCl$ to $CF_2HCF_2Cl$ is below about 0.5:1.

6. The process of claim 1 wherein the composition having said initial mole ratio is provided by hydrogenolysis of $CF_2ClCF_2Cl$.

7. The process of claim 6 wherein $CF_2ClCF_2Cl$ is reacted with hydrogen at a temperature between about 350° C. and 700° C. in a reaction vessel of nickel, iron, cobalt or their alloys which either is empty or is packed with silica, silicon carbide, or low surface area carbon, or with nickel, iron, cobalt or their alloys.

8. The process of claim 1 wherein the hydrogenolysis of the composition is accomplished by reacting the $CF_3CHFCl$ and $CF_2HCF_2Cl$ with hydrogen at a temperature between about 350° C. and 700° C. in a reaction vessel of nickel, iron, cobalt or their alloys which either is empty or is packed with silica, silicon carbide, or low surface area carbon, or with nickel, iron, cobalt or their alloys.

9. A process for producing a mixture of $CF_3CH_2F$ and $CF_2HCF_2H$ from a composition which comprises $CF_2HCF_2Cl$ and has an initial mole ratio of $CF_3CHClF$ to $CF_2HCF_2Cl$ greater than the equilibrium mole ratio of $CF_3HCF_2Cl$ greater than the equilibrium mole ratio of $CF_3CHClF$ to $CF_2HCF_2Cl$ at 475° C. using hydrogenolysis, characterized by decreasing the mole ratio of $CF_3CH_2F$ to $CF_2HCF_2H$ in the product mixture produced from said composition by contacting said composition prior to said hydrogenolysis with a catalyst consisting essentially of a halided aluminum oxide, an aluminum halide, or mixtures thereof for a time sufficient to allow the mole ratio of $CF_3CHFCl$ to $CF_2HCF_2Cl$ in said composition to decrease by substantial interconversion between $CF_3CHFCl$ and $CF_2H CF_2Cl$; and providing during said catalyst contact, a temperature within the range of about 50° C. to 475° C. at which the equilibrium mole ratio of $CF_3CHFCl$ to $CF_2HCF_2 Cl$ is less than said initial mole ratio.

10. A process in accordance with claim 9 for the preparation of a mixture of $CF_3CH_2F$ and $CF_2HCF_2H$ having a selected mole ratio of $CF_3CH_2F$ to $CF_2HCF_2H$ which is equal to or greater than the equilibrium ratio of $CF_3CHFCl$ to $CF_2HCF_2Cl$ at 475° C., including the steps of:

(1) providing a composition comprising $CF_2HCF_2Cl$ wherein the mole ratio of $CF_3CHClF$ to $CF_2HCF_2Cl$ in said composition is greater than said selected mole ratio;

(2) contacting said composition with a catalyst consisting essentially of a halided aluminum oxide, an aluminum halide, or mixtures thereof, for a time sufficient to allow the mole ratio of $CF_3CHFCl$ to $CF_2HCF_2Cl$ in the composition to decrease to said selected mole ratio or less by substantial interconversion between $CF_3CHFCl$ and $CF_2HCF_2Cl$;

(3) providing during said catalyst contact, a temperature within the range of about 50° C. to 475° C. at which the equilibrium mole ratio of $CF_3CHFCl$ to $CF_2HCF_2Cl$ is at most equal to said selected mole ratio;

(4) preparing a mixture of $CF_3CHFCl$ and $CF_2HCF_2Cl$ which comprises said catalyst-contacted composition and has a mole ratio of $CF_3CHFCl$ to $CF_2HCF_2Cl$ equal to said selected mole ratio; and (5) converting the $CF_3CHFCl$ and $CF_2HCF_2Cl$ in said mixture thereof respectively to $CF_3CH_2F$ and $CF_2HCF_2H$ by hydrogenolysis.

11. The process of claim 9 wherein the initial mole ratio of $CF_3CH_2F$ to $CF_2HCF_2H$ is greater than the equilibrium ratio of $CF_3CHFCl$ to $CF_2HCF_2Cl$ at about 130° C.; wherein catalyst contact is accomplished in the liquid phase; wherein the catalyst is an aluminum halide; and wherein the temperature provided during catalyst contact is within the range of 50° C. to about 130° C.

12. The process of claim 9 wherein steps (2) and (3) are accomplished in the gas phase; and wherein the catalyst of step (3) is a halided aluminum oxide.

* * * * *

UNITED STATES PATENT AND TRADEMARK OFFICE
CERTIFICATE OF CORRECTION

PATENT NO. : 5,030,372

DATED : July 9, 1991

INVENTOR(S) : Manogue et al.

It is certified that error appears in the above-identified patent and that said Letters Patent is hereby corrected as shown below:

In the abstract line 7, replace "in" with --is--.

At col. 1, line 22, replace "$CF_3CHClF_2$" with --$CF_3CHClF$--.

At col. 1, line 58, replace "1224a" with --124a--.

At col. 4, line 34, replace "of HFC-134" with --of HFC-134a--.

At col. 4, line 57, replace "$C_2HClF4$" with --$C_2HClF_4$--.

At col. 4, line 58, replace "$C_2HClF4$" with --$C_2HClF_4$--.

At col. 4, line 62, after "the" and before "wherein" insert --mole ratio of $CF_3CHClF$ to $CClF_2CHF_2$ in a composition--.

At col. 5, line 33, replace "Cl3F" with --$CCl_3F$--.

At col. 5, line 44, replace "$Cl_4$" with --$CCl_4$--.

At col. 7, line 7, replace "$CClF_2CHF_z$" with --$CClF_2CHF_2$-- and "$CF_3CFClF$" with --$CF_3CHClF$--.

At col. 7, line 33, replace "$CF_3Cl_3$" with --$CF_3CCl_3$-- and "$Cl_4$" with --$CCl_4$--.

At col. 8, line 13, delete "15".

UNITED STATES PATENT AND TRADEMARK OFFICE
CERTIFICATE OF CORRECTION

PATENT NO. : 5,030,372

DATED : July 9, 1991

INVENTOR(S) : Manogue et al.

It is certified that error appears in the above-identified patent and that said Letters Patent is hereby corrected as shown below:

At col. 8, line 57 replace "catalyst {contacted" with --catalyst-contacted--.

At col. 9, line 7, replace "CF3CHF1" with --CF3CHFCl--.

At col. 9, line 35, replace "CF2CHClF" with --CF3CHClF--.

At col. 10, line 22, replace "CF2HCFzH" with --CF2HCF2H--.

At col. 11, line 29, after "N2" and before "with", insert --to remove air from the reactor and then optionally.

At col. 11, line 55, replace "1/2" with --1/8--.

At col. 13, line 42, after "2%" and before "mL", insert --solution of HCFC-122a in HCFC-122 was then provided @ 2--.

At col. 13, line 59, replace "Cr2o3" with --Cr2O3--.

At col. 14, line 31, replace "Diochlorodi-" with --Dichlorodi--.

At col. 14, line 58, replace "CoCl2Al2O3" with --CoCl2/Al2O3--.

At col. 14, line 61, replace "N2HF" with --N2/HF--.

At col. 15, line 39, replace "Cf3CH2F" with --CF3CH2F--.

UNITED STATES PATENT AND TRADEMARK OFFICE
CERTIFICATE OF CORRECTION

PATENT NO. : 5,030,372

DATED : July 9, 1991

INVENTOR(S) : Manogue et al.

It is certified that error appears in the above-identified patent and that said Letters Patent is hereby corrected as shown below:

At col. 15, line 41, replace "$CF_2CHClF$" with --$CF_3CHClF$--.

At col. 15, line 52, replace "$DV_2CHFCl$" with --$CF_3CHFCl$--.

At col. 16, line 5, replace "$CF_2CHFCl$" with --$CF_3CHFCl$--.

At col. 16, delete line 63.

At col. 17, line 6, replace "$CF_2H\ CF_2Cl$" with --$CF_2HCF_2Cl$--.

Signed and Sealed this

Sixteenth Day of February, 1993

*Attest:*

STEPHEN G. KUNIN

*Attesting Officer*       *Acting Commissioner of Patents and Trademarks*